(12) United States Patent
Chang et al.

(10) Patent No.: US 6,461,592 B1
(45) Date of Patent: Oct. 8, 2002

(54) METHOD FOR TRANSFERRING ONE OR MORE ACTIVE INGREDIENTS BETWEEN DIFFERENT PHASE CARRIERS

(75) Inventors: Hsiu-Kang Chang, Taipei; Huei Lung Chang, Taoyuan Hsien; Tiao Ling Hsieh, Taoyuan Hsien; Chun Hsieh Tsai, Taoyuan Hsien, all of (TW)

(73) Assignee: Purzer Pharmaceutical Co., Ltd. (TW)

( * ) Notice: Subject to any disclaimer, the term of this patent is extended or adjusted under 35 U.S.C. 154(b) by 15 days.

(21) Appl. No.: 09/612,955

(22) Filed: Jul. 10, 2000

(51) Int. Cl.⁷ .............................. B05B 9/00; B05B 9/03; A61K 9/14; A01N 25/08; A01N 25/22
(52) U.S. Cl. ............................ 424/46; 424/43; 424/464; 424/485; 424/78.04; 514/52; 514/912; 128/200.14; 239/338
(58) Field of Search ................................ 424/464, 485, 424/43, 46, 78.04; 514/52, 912; 128/200.14; 239/338

(56) References Cited

U.S. PATENT DOCUMENTS 4,963,367 A  * 10/1990  Ecanow ...................... 424/485
5,698,533 A  * 12/1997  Kang ........................... 514/52

* cited by examiner

Primary Examiner—Frederick Krass
Assistant Examiner—Clinton Ostrup
(74) Attorney, Agent, or Firm—Lowe Hauptman Gilman & Berner, LLP

(57) ABSTRACT

The present invention relates to a method for transferring one or more active ingredients between different phase carriers, which includes: (a) providing a solid, semi-solid, or nonaqueous liquid drug which contains at least one active ingredient; (b) admixing said drug with water or water solution to form an admixture; and (c) nebulizing said admixture to form liquid fine drops containing said active ingredient. This method enables the active ingredient stored in a solid phase carrier to transfer into an aqueous phase carrier, or enables the active ingredient stored in a nonaqueous liquid carrier to transfer into an aqueous phase carrier. The aqueous phase carrier contains the active ingredient can then be nebulized with a nebulizer by means of ultrasonic vibration. The present invention provides a new method for controlling administration by transferring the active ingredient between different phase carriers.

18 Claims, No Drawings

METHOD FOR TRANSFERRING ONE OR MORE ACTIVE INGREDIENTS BETWEEN DIFFERENT PHASE CARRIERS

BACKGROUND OF THE INVENTION

1. Field of the Invention

The present invention relates to a method for controlling administration, particularly to a method for transferring one or more active ingredients between different phase carriers.

2. Description of Related Art

U.S. Pat. No. 5,698,533 discloses "Ophthalmic Pharmaceutical Composition", which provides a method of administering a drug to an eye including the steps of: (a) admixing a pharmaceutically acceptable hydrocarbonaceous semi-solid or oil which contains the drug with water at a temperature above the melting point of the semi-solid or oil; and (b) nebulizing the admixture to form liquid drops; and (c) applying the liquid drops to the eye.

SUMMARY OF THE PRESENT INVENTION

It is an object of the present invention to provide a method, which enables one or more active ingredients to be conveniently transferred between different phase carriers, so that the active ingredient can be stored and used optionally.

It is another object of the present invention to provide a method, which enables one or more active ingredients to be transferred between different phase carriers. For example, the active ingredient unstable in water can be stored in an oil phase carrier (oil phase) or non-aqueous liquid phase carrier to keep the active ingredient stable. When desired to use, then the active ingredient can be transferred to water or water solution (aqueous phase carrier), and then be transferred to liquid fine drops (vapor phase).

It is the other object of the present invention to provide a method, which enables one or more active ingredients stored in a solid phase carrier (solid phase) to be transferred to an aqueous phase carrier, and then be transferred to liquid fine drops (vapor phase).

One aspect of this invention relates to a method for transferring one or more active ingredients between different phase carriers comprising the steps of: (a) providing a solid, semi-solid, or non-aqueous liquid drug which contains at least one active ingredient; (b) admixing said drug with water or water solution to form an admixture; and (c) nebulizing said admixture to form liquid fine drops containing said active ingredients.

The aforesaid solid drug can be a solid active ingredient (or active ingredients) without a carrier, or an active ingredient (or active ingredients) mixed with a solid carrier. The solid drug can be in the form of powder, granule, tablet or capsule, wherein the powder is preferred. In order to control the amount of the active ingredient in the powder, a solid powdered diluent can be added. The solid powdered diluent can be selected from the group consisting of dicalcium phosphate, calcium sulfate, lactose, kaolin, sodium chloride, dry starch, and powdered sugar.

The aforesaid semi-solid drug can be an active ingredient (or active ingredients) mixed with a grease, fat or wax carrier.

The aforesaid non-aqueous liquid drug can be an active ingredient (or active ingredients) stored in a non-aqueous liquid carrier such as oil phase carrier, alcohol carrier, or other organic carriers. The oil phase carrier is not limited here, but must enable the active ingredient to remain stable therein. The oil phase carrier can be animal oil (for example:

lanolin), plant oil (for example: olive oil, corn oil, soybean oil), or mineral oil.

There is no special limitation on the water solution of step (b). Example of the water solution is an aqueous solution containing active ingredients.

The drug of the present invention can be contained one or more active ingredients. The active ingredient is selected from the group consisting of ophthalmic agents, dermal agents (including cosmetic agents), ENT (ear, nose and throat) agents, and respiratory agents.

The ophthalmic agents can be selected from the group consisting of vitamins, steroids (e.g. betamethasone, or dexamethasone), cephalosporins (e.g. cephradine, or cephalexin), penicillins (e.g. amoxicillin, or ampicillin), tetracyclines (e.g. chlorotetracycline, or demeclocycline), macrolides (e.g. erythromycin base, erythromycin propionate), aminoglycosides (e.g. gentamicin, tobramycin or neomycin), sulfonamides (e.g. sulfamethomidin, sulfamethoxypyridazine), polypetides (e.g. bacitracin) and naphazoline hydrochloride.

The dermal agents can be selected from the group consisting of vitamins, steroids (e.g. betamethasone, or dexamethasone), cephalosporins (e.g. cephradine, or cephalexin), penicillins (e.g. amoxicillin, or ampicillin), tetracyclines (e.g. chlorotetracycline, or demeclocycline), macrolides (e.g. erythromycin base, erythromycin propionate), aminoglycosides (e.g. gentamicin, tobramycin or neomycin), sulfonamides (e.g. sulfamethomidin, sulfamethoxypyridazine), polypetides (e.g. bacitracin) hydroquinone, piroxicam, and indomethacin.

The ENT (ear, nose and throat) agents can be selected from the group consisting of vitamins, steroids (e.g. betamethasone, or dexamethasone), cephalosporins (e.g. cephradine, or cephalexin), penicillins (e.g. amoxicillin, or ampicillin), tetracyclines (e.g. chlorotetracycline, or demeclocycline), macrolides (e.g. erythromycin base, erythromycin propionate), aminoglycosides (e.g. gentamicin, tobramycin or neomycin), sulfonamides (e.g. sulfamethomidin, sulfamethoxypyridazine), polypetides (e.g. bacitracin), naphazoline hydrochloride, and acetylcysteine.

The respiratory agents can be selected from the group consisting of vitamins, steroids (e.g. betamethasone, or dexamethasone), cephalosporins (e.g. cephradine, or cephalexin), penicillins (e.g. amoxicillin, or ampicillin), tetracyclines (e.g. chlorotetracycline, or demeclocycline), macrolides (e.g. erythromycin base, erythromycin propionate), aminoglycosides (e.g. gentamicin, tobramycin or neomycin), sulfonamides (e.g. sulfamethomidin, sulfamethoxypyridazine), polypetides (e.g. bacitracin), ephedrine sulfate, methylephedrine, acetylcysteine, isoproterenol sulfate, and aminophylline.

In order to transfer the active ingredient into water after the drug is mixed with water or water solution to form the admixture in the step (b), it may be necessary to stir, oscillate, or heat the admixture.

The nebulizer is a wellknown device and is easily obtained and operated by one skilled in the art. In the present invention, the nebulizer is used for providing energy to oscillate water and form a liquid fine drops escaping from the surface of the admixture (active ingredient with water or water solution). The temperature of the nebulized fine drops of liquid was about 25° C. The active ingredient of the admixture can be brought out with liquid fine drops to achieve the object of controlling drug delivery.

DETAILED DESCRIPTION OF THE PREFERRED EMBODIMENTS

The characteristic of the present invention is the transfer of active ingredients. The method provided in the present invention enables one or more active ingredients stored in a carrier in a certain phase (such as an oil phase carrier, a grease phase carrier, or a solid phase carrier) to transfer into an admixture (water or water solution phase). Then, the active ingredient can be brought out with liquid fine drops (vapor phase) from the admixture by means of ultrasonic vibration.

The present invention can be applied in many situations. For example, the active ingredient (e.g. cephalosporin, vitamin C, or penicillin, etc) unstable in water can be stored in an oil phase carrier, a grease phase carrier, or a solid phase carrier to form a non-aqueous drug to keep the active ingredient stable. When desired to use, then the drug can be mixed with water or water solution to form an admixture. The admixture was then placed in a nebulizer to form fine drops of liquid. The nebulized fine drops of liquid can then be easily and smoothly delivered to the patient's body by gentle currents of air (e.g. provided by a fan installed in the nebulizer).

In general, the oil phase carrier or the grease phase carrier in the admixture is not brought out with liquid fine drops. Only the active ingredient is brought out with liquid fine drops. The method of the present invention enables an active ingredient (or active ingredients) to be conveniently transferred between different phase carriers.

The present invention is demonstrated in more detail with reference to the following examples, which are only illustrative and are not intended to limit the scope of the present invention.

EXAMPLE 1
(The Preparation of a Drug Containing Cephalexin Monohydrate)

10 mg cephalexin monohydrate (an active ingredient) is added into a 10 ml flask, and then mineral oil is added to obtain a 10 ml drug containing 0.1% (W/V) cephalexin monohydrate.

EXAMPLES 2 to 5
(The Preparation of Drugs Containing Cephalexin Monohydrate)

Repeat the steps in example 1, but 50 mg, 100 mg, 250 mg, and 500 mg cephalexin monohydrate are added instead to obtain pharmaceuticals containing 0.5% (W/V), 1.0% (W/V), 2.5% (W/V), and 5.0% (W/V) cephalexin monohydrate respectively.

EXAMPLES 6 and 7
(The Preparation of Drugs Containing Cephalexin Sodium)

Repeat the steps in example 1, but 100 mg and 500 mg cephalexin sodium are respectively added instead to obtain the pharmaceuticals containing 1.0% (W/V) and 5.0% (W/V) cephalexin sodium.

Test Example 1
(Nebulization and HPLC Analysis)

200 μl(V1) drug obtained in example 1 is added into a cup containing 5 ml(V2) water to form an admixture, and then the cup is placed in a nebulizer (Model 8050, Formosa-CJ Business Corp., Taipei, Taiwan) which nebulized the admixture in the cup into liquid fine drops. After nebulized for a period of time, there are some oil phase liquid still remained in the cup, and the liquid fine drops is collected and cooled down to become liquid which is a water solution containing the active ingredient. The concentration of the active ingredient in the collected liquid (liquid fine drops) is then determined by HPLC analysis, and the results are listed in table 1, wherein the term "theoretical concentration" is the concentration of the active ingredient in the admixture before nebulization, and the term "liquid fine drops concentration" is the concentration of the active ingredient in the collected liquid (liquid fine drops).

Test Examples 2 to 7
(Nebulization and HPLC Analysis)

Repeat the steps in test example 1, but the drugs obtained in examples 2 to 7 are respectively added instead, and the results of HPLC analysis are listed in table 1.

TABLE 1

| test example | active ingredient | theoretical concentration (mg/ml) | liquid fine drops concentration (mg/ml) | recovery ratio (%) |
|---|---|---|---|---|
| 1 | cephalexin monohydrate | 0.04 | 0.0302 | 75.38 |
| 2 | cephalexin monohydrate | 0.20 | 0.1635 | 81.74 |
| 3 | cephalexin monohydrate | 0.40 | 0.3889 | 97.23 |
| 4 | cephalexin monohydrate | 1.00 | 0.9614 | 96.14 |
| 5 | cephalexin monohydrate | 2.00 | 1.3847 | 68.74 |
| 6 | cephalexin sodium | 0.40 | 0.3659 | 91.49 |
| 7 | cephalexin sodium | 2.00 | 1.6590 | 82.95 | theoretical concentration=(concentration of drug(% W/V))× (amount of drug(=V1))/(amount of water in the cup(=V2))
recovery ratio (%)=(liquid fine drops concentration)/ (theoretical concentration)×100%

The active ingredient contained in the drug obtained in examples 1 to 7 are all stored in the oil phase carriers. The drugs obtained in examples 1 to 7 are respectively added into water to form 2-phase (oil/aqueous) admixtures. The admixtures can then be conveniently nebulized with a nebulizer by means of ultrasonic vibration. According to results listed in table 1, the active ingredients stored in the drugs (oil phase) can be transferred to the admixtures (oil/aqueous phase), and can then be transferred to liquid fine drops (vapor phase) by nebulizing the admixture with a nebulizer. Additionally, the high recovery ratio (for example in test example 3 the recovery ratio is 97.23%) in the method of the present invention indicate the active ingredients (cephalexin monohydrate and cephalexin sodium) can be easily and effectively transferred between different phases.

EXAMPLE 8
(The Preparation of a 1-phase (Aqueous) Admixture Containing Tobramycin)

15 mg solid tobramycin is added into 5 ml water to obtain an admixture containing 3 mg/ml tobramycin.

EXAMPLE 9
(The Preparation of a 2-phase (Oil/Aqueous) Admixture Containing Tobramycin and Cephalexin Monohydrate)

5 ml water solution containing 3 mg/ml tobramycin is added into a cup for nebulization, and then a 200 μl mixture consisting of 1% (W/V) cephalexin monohydrate in mineral oil is added to obtain a 2-phase (oil/aqueous) admixture containing 3 mg/ml tobramycin and 0.4 mg/ml cephalexin monohydrate.

EXAMPLE 10
(The Preparation of a 2-phase (Oil/Aqueous) Admixture Containing Cephradine Monohydrate and Cephalexin Monohydrate)

5 mg cephradine monohydrate and 5 mg cephalexin monohydrate are added into a 10 ml flask, and then mineral oil is added to the volume obtain a 10 ml oil phase drug containing 0.5% (W/V) cephradine monohydrate and 0.5% (W/V) cephalexin monohydrate in mineral oil. Then 200 $\mu l$(=V1) above oil phase drug is added into a cup containing 5 ml(=V2) water and stirred to form a 2-phase (oil/aqueous) admixture containing 0.2 mg/ml cephradine monohydrate and 0.2 mg/ml cephalexin.

Test Examples 8 to 10
(Nebulization and HPLC Analysis)

Repeat the steps in test example 1, but the admixtures obtained in examples 8 to 10 are respectively added instead, and the results of HPLC analysis are listed in table 2.

TABLE 2

| test example | active ingredient | theoretical concentration (mg/ml) | Liquid fine drops concentration (mg/ml) | recovery ratio (%) |
|---|---|---|---|---|
| 8 | tobramycin | 3 | 2.7668 | 92.23 |
| 9 | tobramycin | 3 | 2.8916 | 96.39 |
|   | cephalexin monohydrate | 0.4 | 0.3323 | 83.07 |
| 10 | cephradine monohydrate | 0.2 | 0.1535 | 76.74 |
|   | cephalexin monohydrate | 0.2 | 0.1948 | 97.40 |

In example 8, the active ingredient (tobramycin) stored in the solid phase carrier transfers into the aqueous phase carrier after adding water for preparing the admixture. The result of test example 8, as listed in table 2, indicates the drug obtained in example 8 can be nebulized to form liquid fine drops by the nebulizer. According to results listed in table 2, the collected liquid (collected from liquid fine drops) containing the active ingredient (tobramycin). Additionally, the high recovery of 92.23% indicates the active ingredient (tobramycin) stored in a solid phase carrier can be successfully transferred to vapor phase (liquid fine drops).

In example 9, another active ingredient (cephalexin monohydrate) stored in an oil phase carrier is added into the admixture of example 8 to form a 2-phase (oil/aqueous) admixture. The result of test example 9, as listed in table 2, indicates that the active ingredient (cephalexin monohydrate) stored in the oil phase carrier and the active ingredient (tobramycin) stored in the aqueous phase carrier can be mixed to obtain the 2-phase (oil/aqueous) admixture, and then be nebulized into liquid fine drops. The collected liquid (liquid fine drops) is water solution primarily containing the active ingredients (tobramycin and cephalexin monohydrate). Both recovery ratios over 80% indicate that the mixture of the active ingredients stored in the aqueous phase carrier and in the oil phase carrier can be transferred to vapor phase (liquid fine drops).

In example 10, the admixture is prepared by adding the drug (cephradine monohydrate and cephalexin monohydrate stored in the oil phase carrier) into water. The result of test example 10, as listed in table 2, indicates that the admixture can form liquid fine drops by nebulization, and the collected liquid (liquid fine drops) is water solution primarily containing the active ingredients (cephradine monohydrate and cephalexin monohydrate), so that two active ingredients stored in oil phase carrier can be transferred to vapor phase (liquid fine drops).

From the foregoing description, one skilled in the art can easily ascertain the essential characteristics of this invention, and, without departing from the scope thereof, can make various changes and modifications of the invention to adapt it to various usages and conditions. Thus, other embodiments are also within the claims.

What is claimed is:

1. A method for transferring an active ingredient from a solid phase to an aqueous liquid phase comprising:

(a) providing a solid phase containing at least one solid active ingredient and at least one solid carrier or diluent material;

(b) admixing said solid phase with an aqueous liquid comprising water to form an admixture; and (c) nebulizing said admixture under conditions sufficient to transfer substantially only solid active ingredient(s) from said solid phase to said aqueous liquid phase and to form fine drops of said aqueous liquid phase containing said active ingredient(s) while not transferring a substantial amount of said solid carrier or diluent to said fine drops of aqueous liquid.

2. The method of claim 1, wherein said solid phase contains at least two active ingredients.

3. The method of claim 1, wherein said admixture contains two or more active ingredients.

4. The method of claim 1, wherein said admixture is nebulized by a nebulizer.

5. The method of claim 1, wherein a recovery rate of the solid drug is greater than 90%.

6. The method of claim 1, wherein the solid active ingredient is tobramycin.

7. The method of claim 1, wherein said solid phase is selected from the group consisting of powder, granule, tablet and capsule.

8. The method of claim 7, wherein said solid phase is a powder, said powder contains at least one active ingredient and at least one solid carrier or diluent material, said powder is agitatingly admixed with said aqueous phase, and said agitated admixture is subjected to nebulizing.

9. The method of claim 8, wherein said powder is selected from the group consisting of dicalcium phosphate, calcium sulfate, lactose, kaolin, sodium chloride, dry starch, and powdered sugar.

10. The method of claim 1, wherein said active ingredient is selected from respiratory agents.

11. The method of claim 10, wherein said respiratory agent is selected from the group consisting of vitamins, steroids, cephalosporins, penicillins, tetracyclines, macrolides, aminoglycosides, sulfonamides, polypetides, ephedrine sulfate, methylephedrine, acetylcyseine, isoproterenol sulfate, and aminophylline.

12. A method for preparing fine drops of an aqueous liquid containing at least one solid active material adapted for use in treating a resiratory ailment, comprising:

(a) providing a solid phase which contains at least one active solid ingredient and at least one solid carrier or diluent material;

(b) admixing said solid phase with an aqueous liquid comprising water to form an admixture; and (c) nebulizing said admixture under conditions sufficient to transfer substantially only solid active ingredient(s) from said solid phase to said aqueous liquid phase and to form fine drops of said aqueous liquid phase containing said active ingredient(s) while not transferring a substantial amount of solid other than said solid active ingredient to said fine drops of aqueous liquid.

13. The method of claim 12, wherein said active solid ingredient is at least one member selected from the group consisting of vitamins, steroids, cephalosporins, penicillins, tetracyclines, macrolides, aminoglycosides, sulfonamides, polypetides, ephedrine sulfate, methylephedrine, acetylcyseine, isoproterenol sulfate and aminophylline.

14. The method of claim 12, wherein a recovery rate of the solid drug is greater than 90%.

15. The method of claim 12, wherein the solid active ingredient is tobramycin.

16. The method of claim 12, wherein said solid phase is selected from the group consisting of powder, granule, tablet and capsule.

17. The method of claim 16, wherein said solid phase is a powder, said powder contains at least one active ingredient and at least one solid carrier or diluent.

18. The method of claim 17, wherein said solid carrier or diluent is at least one member selected from the group consisting of dicalcium phosphate, calcuim sulfate, lactose, kaolin, sodium chloride, dry starch and powdered sugar.

* * * * *